US008326555B2

(12) United States Patent
Morgan

(10) Patent No.: US 8,326,555 B2
(45) Date of Patent: Dec. 4, 2012

(54) SYSTEM AND METHOD FOR MEASURING CONDUCTIVITY/RESISTIVITY OF WATER HAVING HIGH PURITY

(75) Inventor: John W. Morgan, Hillsboro, OR (US)

(73) Assignee: Georg Fischer Signet LLC, El Monte, CA (US)

( * ) Notice: Subject to any disclaimer, the term of this patent is extended or adjusted under 35 U.S.C. 154(b) by 248 days.

(21) Appl. No.: 12/877,869

(22) Filed: Sep. 8, 2010

(65) Prior Publication Data

US 2011/0218750 A1 Sep. 8, 2011

Related U.S. Application Data

(60) Provisional application No. 61/276,068, filed on Sep. 8, 2009.

(51) Int. Cl.
G06F 19/00 (2011.01)
G01R 27/08 (2006.01)

(52) U.S. Cl. ............... 702/65; 702/57; 702/99; 702/130; 702/189; 324/439; 324/440; 324/441; 324/693; 73/25.03

(58) Field of Classification Search ............... 702/45, 702/50, 57, 65, 99, 130, 189, 194; 324/439–450, 324/693; 73/25.03, 335.05
See application file for complete search history.

(56) References Cited

U.S. PATENT DOCUMENTS

| 3,870,033 | A | 3/1975 | Faylor et al. |
| 5,326,035 | A | 7/1994 | Ohmi et al. |
| 5,385,664 | A | 1/1995 | Oinuma et al. |
| 5,868,924 | A | 2/1999 | Nachtman et al. |
| 5,954,965 | A | 9/1999 | Kubota et al. |
| 6,733,661 | B2 | 5/2004 | Mukogawa et al. |
| 7,550,979 | B2 * | 6/2009 | Zhou et al. ............ 324/693 |
| 2003/0011386 | A1 * | 1/2003 | Xie et al. ............ 324/694 |
| 2007/0018650 | A1 | 1/2007 | Bhansali et al. |
| 2009/0085583 | A1 | 4/2009 | Waid et al. |

FOREIGN PATENT DOCUMENTS

| EP | 0 582 329 | 2/1994 |
| JP | 2002-062275 | 2/2002 |

OTHER PUBLICATIONS

Bevilacqua, Anthony C., et al., "Advances in Resistivity Instrumentation for UPW Systems of the Future", (Mar. 1, 2000), pp. 1-15.
Bevilacqua, Anthony C., et al., "The Effect of Temperature, Temperature Error, and Impuritieson Compensated Resistivity Measurements", (Mar. 1, 1997), pp. 1-16.
Bevilacqua, Anthony C., "Ultrapure Water—The Standard for Resistivity Measurementsof Ultrapure Water", (Mar. 2, 1998), pp. 1-25.

* cited by examiner

Primary Examiner — Sujoy Kundu
(74) Attorney, Agent, or Firm — Tsircou Law, P.C.

(57) ABSTRACT

A system and related method are provided for measuring conductivity/resistivity of water having high purity, including a temperature sensor and a conductivity/resistivity sensor exposed to a water source. The system further includes a computing assembly configured to receive measurement signals from the sensors and to determine change in resistivity over a change in temperature (a collected R/T slope) from the collected temperature measurements and the collected resistivity measurements. The system compares the collected R/T slope to a standardized R/T slope at a temperature value corresponding to a midpoint temperature of the temperature measurements over the prescribed time interval. Based on the comparing, the system provides providing a compensated measurement for resistivity or conductivity of the water source. As a result, the system can calibrate the sensor continually during use, in real time, resulting in highly improved accuracy.

19 Claims, 10 Drawing Sheets

| Temp | uS/cm Pure H2O | uS/cm 0.0001 | uS/cm 0.0002 | uS/cm 0.0003 | uS/cm 0.0004 | uS/cm 0.0005 | uS/cm 0.0006 | uS/cm 0.0007 | uS/cm 0.0008 | uS/cm 0.0009 | uS/cm 0.001 | uS/cm 0.0011 | uS/cm 0.0012 | uS/cm 0.0013 | uS/cm 0.0014 | uS/cm 0.0015 |
|---|---|---|---|---|---|---|---|---|---|---|---|---|---|---|---|---|
| 21.40 | 22.06 | 22.02 | 21.97 | 21.92 | 21.87 | 21.82 | 21.78 | 21.73 | 21.68 | 21.63 | 21.59 | 21.54 | 21.49 | 21.45 | 21.40 | 21.36 |
| 21.42 | 22.05 | 22.00 | 21.95 | 21.90 | 21.85 | 21.81 | 21.76 | 21.71 | 21.66 | 21.62 | 21.57 | 21.52 | 21.48 | 21.43 | 21.39 | 21.34 |
| 21.43 | 22.03 | 21.98 | 21.93 | 21.88 | 21.84 | 21.79 | 21.74 | 21.69 | 21.65 | 21.60 | 21.55 | 21.51 | 21.46 | 21.41 | 21.37 | 21.32 |
| 21.45 | 22.01 | 21.96 | 21.91 | 21.87 | 21.82 | 21.77 | 21.72 | 21.68 | 21.63 | 21.58 | 21.54 | 21.49 | 21.44 | 21.40 | 21.35 | 21.31 |
| 21.46 | 21.99 | 21.94 | 21.90 | 21.85 | 21.80 | 21.75 | 21.71 | 21.66 | 21.61 | 21.56 | 21.52 | 21.47 | 21.43 | 21.38 | 21.33 | 21.29 |
| 21.48 | 21.97 | 21.93 | 21.88 | 21.83 | 21.78 | 21.73 | 21.69 | 21.64 | 21.59 | 21.55 | 21.50 | 21.45 | 21.41 | 21.36 | 21.32 | 21.27 |
| 21.49 | 21.96 | 21.91 | 21.86 | 21.81 | 21.76 | 21.72 | 21.67 | 21.62 | 21.58 | 21.53 | 21.48 | 21.44 | 21.39 | 21.35 | 21.30 | 21.26 |
| 21.51 | 21.94 | 21.89 | 21.84 | 21.79 | 21.75 | 21.70 | 21.65 | 21.61 | 21.56 | 21.51 | 21.47 | 21.42 | 21.37 | 21.33 | 21.28 | 21.24 |
| 21.52 | 21.92 | 21.87 | 21.82 | 21.78 | 21.73 | 21.68 | 21.63 | 21.59 | 21.54 | 21.50 | 21.45 | 21.40 | 21.36 | 21.31 | 21.27 | 21.22 |
| 21.54 | 21.90 | 21.85 | 21.81 | 21.76 | 21.71 | 21.66 | 21.62 | 21.57 | 21.52 | 21.48 | 21.43 | 21.39 | 21.34 | 21.29 | 21.25 | 21.20 |
| 21.55 | 21.88 | 21.84 | 21.79 | 21.74 | 21.69 | 21.65 | 21.60 | 21.55 | 21.51 | 21.46 | 21.41 | 21.37 | 21.32 | 21.28 | 21.23 | 21.19 |
| 21.57 | 21.87 | 21.82 | 21.77 | 21.72 | 21.68 | 21.63 | 21.58 | 21.54 | 21.49 | 21.44 | 21.40 | 21.35 | 21.31 | 21.26 | 21.22 | 21.17 |
| 21.58 | 21.85 | 21.80 | 21.75 | 21.70 | 21.66 | 21.61 | 21.56 | 21.52 | 21.47 | 21.43 | 21.38 | 21.33 | 21.29 | 21.24 | 21.20 | 21.15 |
| 21.60 | 21.83 | 21.78 | 21.73 | 21.69 | 21.64 | 21.59 | 21.55 | 21.50 | 21.45 | 21.41 | 21.36 | 21.32 | 21.27 | 21.23 | 21.18 | 21.14 |
| 21.61 | 21.81 | 21.76 | 21.72 | 21.67 | 21.62 | 21.58 | 21.53 | 21.48 | 21.44 | 21.39 | 21.35 | 21.30 | 21.26 | 21.21 | 21.17 | 21.12 |
| 21.63 | 21.79 | 21.75 | 21.70 | 21.65 | 21.61 | 21.56 | 21.51 | 21.47 | 21.42 | 21.37 | 21.33 | 21.28 | 21.24 | 21.19 | 21.15 | 21.10 |
| 21.64 | 21.78 | 21.73 | 21.68 | 21.63 | 21.59 | 21.54 | 21.49 | 21.45 | 21.40 | 21.36 | 21.31 | 21.27 | 21.22 | 21.18 | 21.13 | 21.09 |
| 21.66 | 21.76 | 21.71 | 21.66 | 21.62 | 21.57 | 21.52 | 21.48 | 21.43 | 21.39 | 21.34 | 21.29 | 21.25 | 21.20 | 21.16 | 21.11 | 21.07 |
| 21.67 | 21.74 | 21.69 | 21.65 | 21.60 | 21.55 | 21.51 | 21.46 | 21.41 | 21.37 | 21.32 | 21.28 | 21.23 | 21.19 | 21.14 | 21.10 | 21.05 |
| 21.68 | 21.72 | 21.67 | 21.63 | 21.58 | 21.53 | 21.49 | 21.44 | 21.40 | 21.35 | 21.31 | 21.26 | 21.22 | 21.17 | 21.13 | 21.08 | 21.04 |
| 21.70 | 21.70 | 21.66 | 21.61 | 21.56 | 21.52 | 21.47 | 21.43 | 21.38 | 21.33 | 21.29 | 21.24 | 21.20 | 21.15 | 21.11 | 21.06 | 21.02 |
| 21.71 | 21.69 | 21.64 | 21.59 | 21.55 | 21.50 | 21.45 | 21.41 | 21.36 | 21.32 | 21.27 | 21.23 | 21.18 | 21.14 | 21.09 | 21.05 | 21.00 |
| 21.73 | 21.67 | 21.62 | 21.58 | 21.53 | 21.48 | 21.44 | 21.39 | 21.34 | 21.30 | 21.25 | 21.21 | 21.16 | 21.12 | 21.07 | 21.03 | 20.99 |
| 21.74 | 21.65 | 21.60 | 21.56 | 21.51 | 21.46 | 21.42 | 21.37 | 21.33 | 21.28 | 21.24 | 21.19 | 21.15 | 21.10 | 21.06 | 21.01 | 20.97 |
| 21.76 | 21.63 | 21.59 | 21.54 | 21.49 | 21.45 | 21.40 | 21.36 | 21.31 | 21.27 | 21.22 | 21.17 | 21.13 | 21.09 | 21.04 | 21.00 | 20.95 |
| 21.77 | 21.62 | 21.57 | 21.52 | 21.48 | 21.43 | 21.38 | 21.34 | 21.29 | 21.25 | 21.20 | 21.16 | 21.11 | 21.07 | 21.02 | 20.98 | 20.94 |
| 21.79 | 21.60 | 21.55 | 21.50 | 21.46 | 21.41 | 21.37 | 21.32 | 21.28 | 21.23 | 21.19 | 21.14 | 21.10 | 21.05 | 21.01 | 20.96 | 20.92 |
| 21.80 | 21.58 | 21.53 | 21.49 | 21.44 | 21.40 | 21.35 | 21.30 | 21.26 | 21.21 | 21.17 | 21.12 | 21.08 | 21.04 | 20.99 | 20.95 | 20.90 |

FIG. 9

SYSTEM AND METHOD FOR MEASURING CONDUCTIVITY/RESISTIVITY OF WATER HAVING HIGH PURITY

CROSS REFERENCE TO RELATED APPLICATION

This application claims priority to U.S. Prov. App. No. 61/276,068, filed Sep. 8, 2009, which is incorporated by reference for all purposes.

FIELD OF THE INVENTION

The present invention relates generally to systems and methods for measuring resistivity/conductivity of fluids and, more particularly, to systems and methods for calibrating resistivity sensors during use, to include usage in measuring resistivity/conductivity of water having high levels of purity to assess contamination levels.

BACKGROUND OF THE INVENTION

Water ($H_2O$) is a strong and aggressive solvent that interacts with and dissolves most substances it meets. Contaminants include atmospheric gases (oxygen, nitrogen, and carbon dioxide), dissolved minerals and organic substances, and suspended colloidal matter. Water also provides an ideal environment for the growth of bacteria and other microorganisms if the necessary nutrients and conditions for growth exist. As a result, all water in nature contains impurities, such as minerals, salts, various metals, and other compounds. In fact, drinking water can be a beneficial source of various compounds. However, in other uses, impure water is an issue. The purity of water can be tested by measuring the resistivity/conductivity of the water.

Electrical conductivity is a measure of a material's ability to conduct an electric current. Resistivity, the reciprocal of conductivity, is the measure of how strongly a material opposes the flow of electric current. Accordingly, a resistivity value can be determined from a conductivity value, and vice versa.

An electrical current results from the motion of electrically charged particles in response to forces that act on them from an applied electric field. Ultra pure water is a low conductor of electricity because it has a small number of electrically charged particles that can flow in response to an electric field. It has a very low conductivity of $5.5 \times 10^{-6}$ S/m. When water is impure, it has a significant number of charged particles, free ions, dissolved in solution. These particles move in response to an applied electric field, and as a result, this makes impure water a good conductor of electricity. Therefore, a measure of the purity of water can be obtained through the measurement of its conductivity/resistivity values. The higher its conductivity and the lower its resistivity, the more impure the water sample is.

Depending on the type and concentration of contaminants, most natural waters are not suitable for potable use much less for most research and industrial applications. Most all municipalities and other purveyors of potable water provide some level of water treatment to make the water suitable for consumption.

Potable water is too contaminated for many applications. Instead, even more highly purified water is required. For example, high-purity water and/or ultra-pure water are typically produced and used in, but not limited to, the following industries: microelectronics manufacturing, semiconductor manufacturing, pharmaceutical manufacturing, photovoltaic manufacturing, power generation Industry, nuclear industry, chemical laboratories, and hospitals.

In selected applications, the purity requirements are very high. Water used in manufacturing electronic components, must be substantially free of extraneous minerals, particles, organisms, organics and dissolved gases. Water purity requirements specified by some semiconductor manufacturers have reached particularly demanding standards. For example, in terms of mass, required purity standards correlate to contaminant levels at or below microgram (µg) levels per liter of water. Exemplary requirements can be found from ASTM International, which provides listing of standards for water purity, among other things, including ASTM D5127-07, entitled "Standard Guide for Ultra-Pure Water Used in the Electronics and Semiconductor Industries," which is herein incorporated by reference, for all purposes.

To purify water to such exacting standards, various treatment processes can be used synergistically, to include filtration, membrane separation, ion exchange, degasification, UV sterilization, and UV oxidation of dissolved organics, to name a few. In each of these processes, measurements are taken of the water stream as it progresses through the process. As a result, one can ensure that the system is functioning properly.

Water must be constantly monitored during the purification process to check the purity of the water at different stages of the process and ensure that the purification process is working. One chemical process that is employed to purify water is the ion-exchange process. In this process, water is filtered through ion-exchange resin or ion-exchange polymer beads, which contain certain ions on their surface. As the water flows over the beads, the impurities in the water are picked up by the beads, which then release the ions on their surface into the water. High purity water can be produced using ion-exchange processes or combinations of membrane and ion-exchange methods. Cations are replaced with hydrogen ions using cation-exchange resins; anions are replaced with hydroxyls using anion-exchange resins. The hydrogen ions and hydroxyls recombine producing water molecules. Thus, no ions remain in the produced water. The purification process is usually performed in several steps with "mixed bed ion-exchange columns" at the end of the technological chain.

As the hydrogen and hydroxyl ions on the resins are displaced by the ions in the water being filtrated, the process reaches equilibrium with a much lower ion concentration in the water than was started with. At this point, no more ions are filtered out of the water by the resins, and the ions "breakthrough" the ion exchange resin.

Because of this "breakthrough" effect, the conductivity/resistivity of the water must be continuously monitored to ensure the purity of the filtered water. If equilibrium is reached and an unmitigated "breakthrough" effect occurs, the water is no longer pure and contamination of the downstream processes occurs.

There are several methods and instruments for examining resistivity/conductivity of water, but these contain several limitations. Technical problems and limitations still exist in resistivity/conductivity instrumentation. For example, such sensors produce measurements that vary slightly from one to the other, even when measuring the same solution at the same time, even with the same sensor model from the same manufacturer. Such variations can result from minor variations in construction, materials, and so on. To account for such variations and improve accuracy, the sensors are calibrated in the factory, where an offset value or cell constant is determined for the sensor.

In measuring water having high levels of purity, sensor error becomes a significant, limiting factor on accuracy. Currently, typical resistivity sensors have an upper limit in accuracy around one to two percent (1%-2%) over the instrument range. As a result, existing resistivity/conductivity instruments can and often do output values that are beyond theoretically capable values. Further, current sensor systems are unable to calibrate conductivity instrumentation in the field; existing instruments are typically factory calibrated.

However, after repeated use, the instrumentation will lose its calibration and accuracy, and field calibration is necessary and more cost-effective than the purchase of new instrumentation. Sometimes such instruments would provide output readings that exceed "theoretical" values of resistivity for theoretically pure water (e.g., ≈ greater than 18.1 mega-ohm (mΩ) at 25 degrees Celsius). Such measurement inaccuracies can limit the effectiveness of purification processes as well as increase associated costs.

It should be appreciated that there remains a need for a system and related method improved sensor systems for accurately measuring resistivity of highly pure water. The present invention fulfills this need and others.

SUMMARY OF THE INVENTION

Briefly, and in general terms, a system and related method are provided for measuring conductivity/resistivity of water having high purity, including a temperature sensor and a conductivity/resistivity sensor exposed to a water source. The system further includes a computing assembly configured to receive measurement signals from the sensors and to determine change in resistivity over a change in temperature (a collected R/T slope) from the collected temperature measurements and the collected resistivity measurements. The system compares the collected R/T slope to a standardized R/T slope at a temperature value corresponding to a midpoint temperature of the temperature measurements over the prescribed time interval. Based on the comparing, the system provides providing a compensated measurement for resistivity or conductivity of the water source. As a result, the system can calibrate the sensor continually during use, in real time, resulting in highly improved accuracy.

In a detailed aspect of an exemplary embodiment, a resistivity offset value is determined as the difference between the midpoint for resistivity ($R_{mid}$) and a theoretical value for resistivity ($R_{theory}$), which determined based on the comparing of the collected R/T slope to a standardized R/T slope.

In another detailed aspect of an exemplary embodiment, the collected R/T slope is determined using a linear regression on the collected measurements. The collected measurements can be filtered to exclude errant data by discarding collected measurements in which the temperature measurement is outside of a prescribed range from the midpoint temperature, resulting in a filtered data set. The collected R/T slope can be determined using a linear regression on the filtered data set More specifically, by example and not limitation, an exemplary method in accordance with the invention is provided including the following:

collecting temperature measurements and resistivity measurements over a prescribed time interval from a temperature sensor and a resistivity sensor exposed to a water source, in which temperature measurements and resistivity measurements are associated together by time;

determining midpoint measurements for resistivity ($R_{mid}$) and temperature ($T_{mid}$) over the prescribed time interval;

filtering out errant data from the collected temperature and resistivity measurements by discarding associated, collected measurements in which the collected temperature is outside of a prescribed temperature range, resulting in a filtered data set;

determining a collected R/T slope from the filtered data set, in which the collected R/T slope is indicative of the change in resistivity versus change in temperature as measured over the prescribed time interval;

comparing the collected R/T slope to a standardized R/T slope at a temperature value corresponding to a midpoint temperature of the temperature measurements over the prescribed time interval; and providing compensated measurements for resistivity or conductivity of the water source based on the comparing.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which:

FIG. 9 is an exemplary table chart depicting theoretical resistivity values in relation to temperature and conductivity attributable to contamination.

DETAILED DESCRIPTION OF THE PREFERRED EMBODIMENTS

Figure 1:
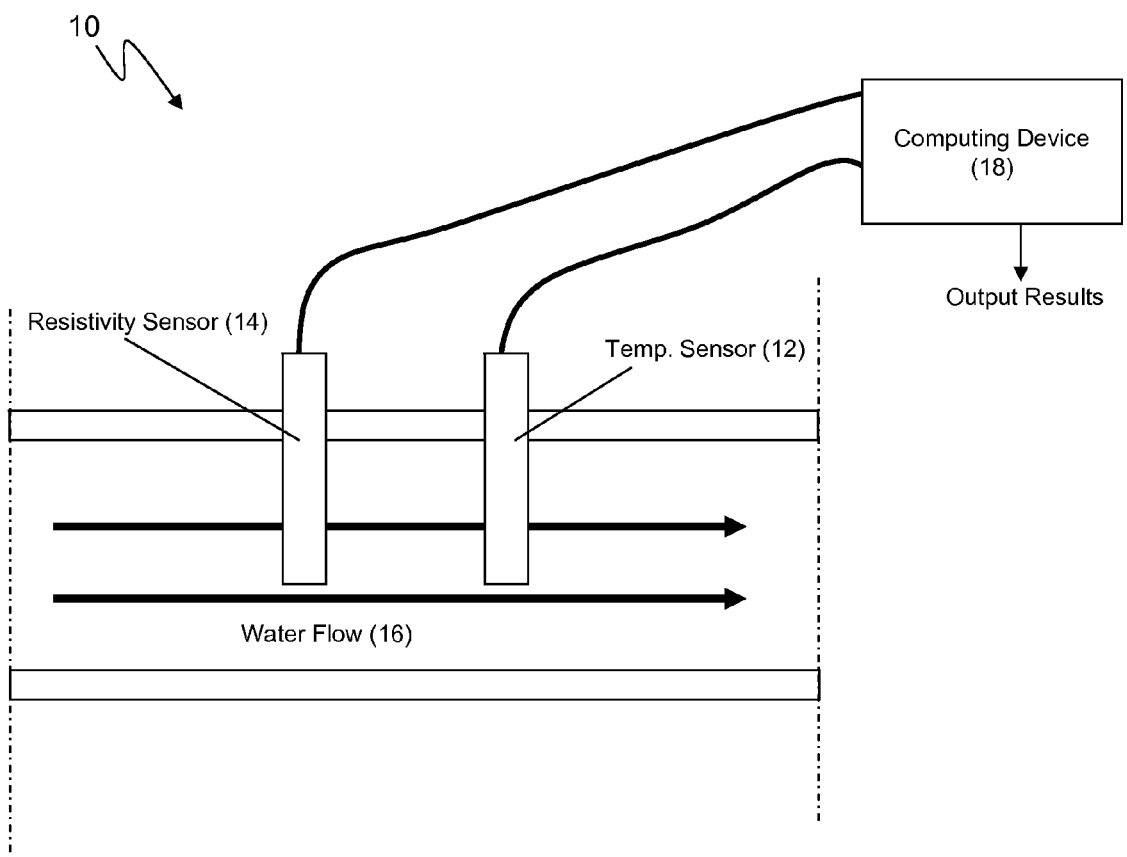
FIG. 1 is a perspective view of an embodiment of a system for measuring resistivity of a fluid in accordance with the present invention, depicting a temperature sensor and a resistivity sensor exposed to a water source.

For convenience of reference, the terms "resistivity" and "conductivity" are used throughout, without repeated reference as to their reciprocal relationship. However, unless otherwise specified, reference to either "resistivity" or "conductivity" is intended also to refer the corresponding reciprocal term.

Various measurements, theoretical values, standardized values, and others, including tables, are provided herein for purposes of illustration only, and are not intended to be limiting, unless otherwise specified.

Referring now to the drawings, there is shown a system 10 for measuring conductivity/resistivity of water having high purity. The system includes a temperature sensor 12 and a conductivity/resistivity sensor (resistivity sensor 14) exposed to a water source 16 to measure temperature and resistivity continuously and in real time. The system further includes a computing assembly 18 configured to receive measurement signals from the sensors, from this data the system can monitor and update the offset value for the resistivity sensor in real time, during use. Thus, the resistivity sensor can be calibrating continually during use, in real time, resulting in highly improved accuracy.

The computing assembly 18 tracks the "collected" temperature and resistivity measurements over time received from the temperature sensor 12 and the resistivity sensor 14. The computing assembly also has access to "theoretical," or otherwise standardized, information that correlates resistivity, conductivity, and R/T slope values for highly pure water across a range of temperatures and at various levels of contamination. The system applies a methodology for comparing the collected measurements to the theoretical values. Based on this comparison, the system updates the offset value of the resistivity sensor and/or otherwise provides calibrated and highly accurate measurements indicating the level of contamination of the water source 16.

Figure 2:
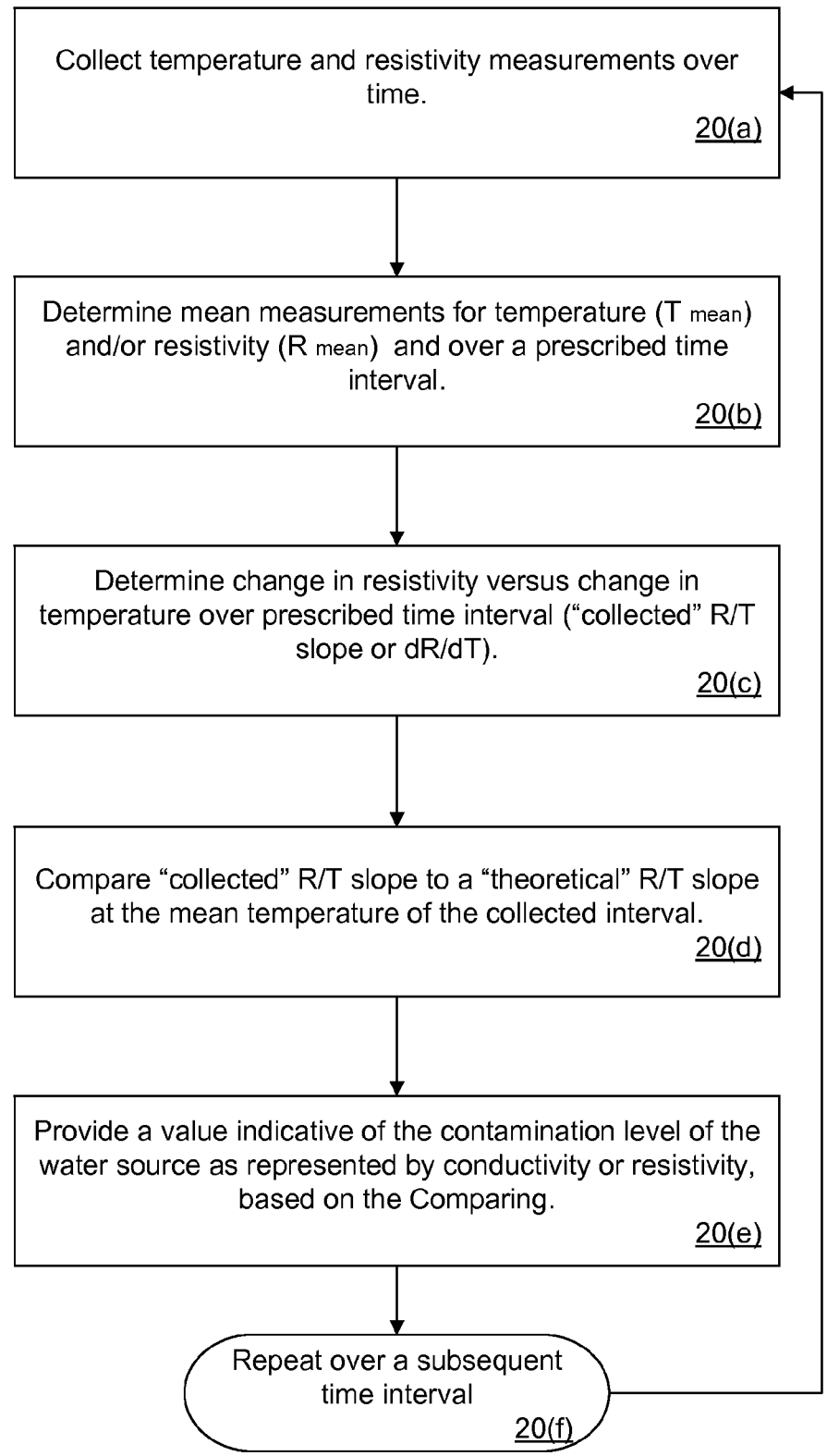
FIG. 2 is simplified flow chart for a first measuring methodology of the system of FIG. 1.

Referring now to FIG. 2, utilizing the computing assembly 18, the system performs several steps 20 for measuring and determining level of contamination of the water source 16, including (a) collecting temperature and resistivity measurements over a prescribed time interval; (b) determining midpoint measurements for temperature ($T_{mid}$) and/or resistivity ($R_{mid}$) over the prescribed time interval; (c) determining a change in resistivity versus change in temperature over for the measurements the prescribed time interval, referred to herein as "collected" R/T slope or dR/dT, (d) comparing the "collected" R/T slope to a "theoretical" change in resistivity versus change in temperature, referred to as "theoretical" (or standardized) R/T slope or dR/dT, (e) determining and outputting a calibrated value indicative of the contamination level of the water source, based on the comparing, and (f) repeating from step (a) over a subsequent time interval.

At Step 20(a), the computing assembly 18 receives measurement data from the temperature sensor 12 and the resistivity sensor 14. This data is captured such that resistivity data points and temperature data points are correlated with respect to time of measurement. In the exemplary embodiment, these data points are uncompensated for temperature. However, in other embodiments, compensated data can be captured and used, in lieu of or in addition to the raw data.

In the exemplary embodiment, the computing assembly 18 is connected to the temperature sensor 12 and the resistivity sensor 14 by wired connections. However, in other embodiments, any other means of transmitting data can be used, such as, wireless communication, the Internet, and other network connections, among others. In this manner, the computing assembly can be remotely located, if desired.

At Step 20(b), the system determines midpoint values for resistivity ($R_{mid}$) and temperature ($T_{mid}$) from the collected measurement over a prescribed time interval. The midpoint value(s) (or midpoint measurement(s)) can be determined by calculating the mean, median, or other values representative of the measured data over the prescribed time interval.

In the exemplary embodiment, midpoint measurements are calculated prior to disposing of data; however, the midpoint can be determined or recalculated after disposing of errant data, without departing from the invention.

The computing assembly 18 can further analyze the collected temperature measurements over the prescribed time interval to determine a filtering factor ("X"). The filtering factor ("X") is correlated to the overall temperature range collected over the prescribed time interval and is used to exclude 'noise' measurements. In the exemplary embodiment, the filtering factor is determined based on a standard deviation determination from the midpoint temperature. The system filters out data that is outside of a prescribed range. More particularly, Where the measured temperature spread is greater than "X", the system filters out data where the temperature is less than ($T_{mid}$–X) or greater than ($T_{mid}$–X), where "X" is determined based on the data set, resulting in a filtered data set of collected temperature measurements and resistivity measurements. In addition or alternatively, the system can forego or otherwise exclude the step of filtering data.

At Step 20(c), the filtered data set is used to determine a change in resistivity versus change in temperature over the prescribed time interval ("collected" R/T slope or dR/dT). The system uses a numerical linear regression technique to calculate the collected R/T slope (dR/dT), based on the filtered data set. In the exemplary embodiment, least squares linear regression model is used, however other approaches for calculating a slope value can be used. In other embodiments, the collected R/T slope (dR/dT) can be determined without using a filtered data set. The collected R/T slope is associated with the midpoint temperature measurement ($T_{mid}$).

For example, and not limitation, a filtered data set of temperature measurements and associated resistivity measurements can be gathered for one minute at 0.25 second intervals. The midpoint temperature ($T_{mid}$) and the mean resistivity ($R_{mid}$) of the data set are determined. The data set is then filtered. Next, the collected R/T slope is determined using a least squares linear regression model on the filtered data set. In this manner, the collected R/T slope, midpoint temperature ($T_{mid}$), and the midpoint resistivity ($R_{mid}$) can be determined over the measured time.

At Step 20(d), the computing assembly 18 identifies theoretical (or standardized) R/T slopes at the temperature determined as the midpoint temperature ($T_{mid}$) of the collected data set of Step 20(b). The theoretical (or standardized) values, referenced herein throughout, can be stored in digital memory (not shown) within or otherwise accessible to the computing assembly. The computing assembly can be configured to calculate the theoretical (or standardized) values. The theoretical (or standardized) values can be derived from calculations, industry standards, algorithms, and/or empirical evidence.

For example, theoretical (or standardized) values can be determined, based upon equations relating to the resistivity of theoretical pure water ($R_{tpw}$) as effected by temperature and theoretical values for resistivity at various levels of contamination ($R_{theory}$), as follows:

$$R_{tpw} = \exp(a_0 + a_1 T + a_2 T^2 + a_3 T^3 + a_4 T^4 + a_5 T^5); \text{ and}$$

$$R_{theory}=1/[(C_{tca})+(1/R_{tpw})]$$

where:

$a_0 = 4.456556$ $a_1 = -7.33064 \times 10^{-2}$ $a_2 = 5.02097 \times 10^{-4}$ $a_3 = -2.56203 \times 10^{-6}$ $a_4 = 6.43445 \times 10^{-9}$ $a_5 = 1.40405 \times 10^{-12}$ T=Temperature (Celsius)

$C_{tca}$=Conductivity (μS/cm) attributable to a 'theoretical' contamination level added to theoretically pure water.

Figure 3:
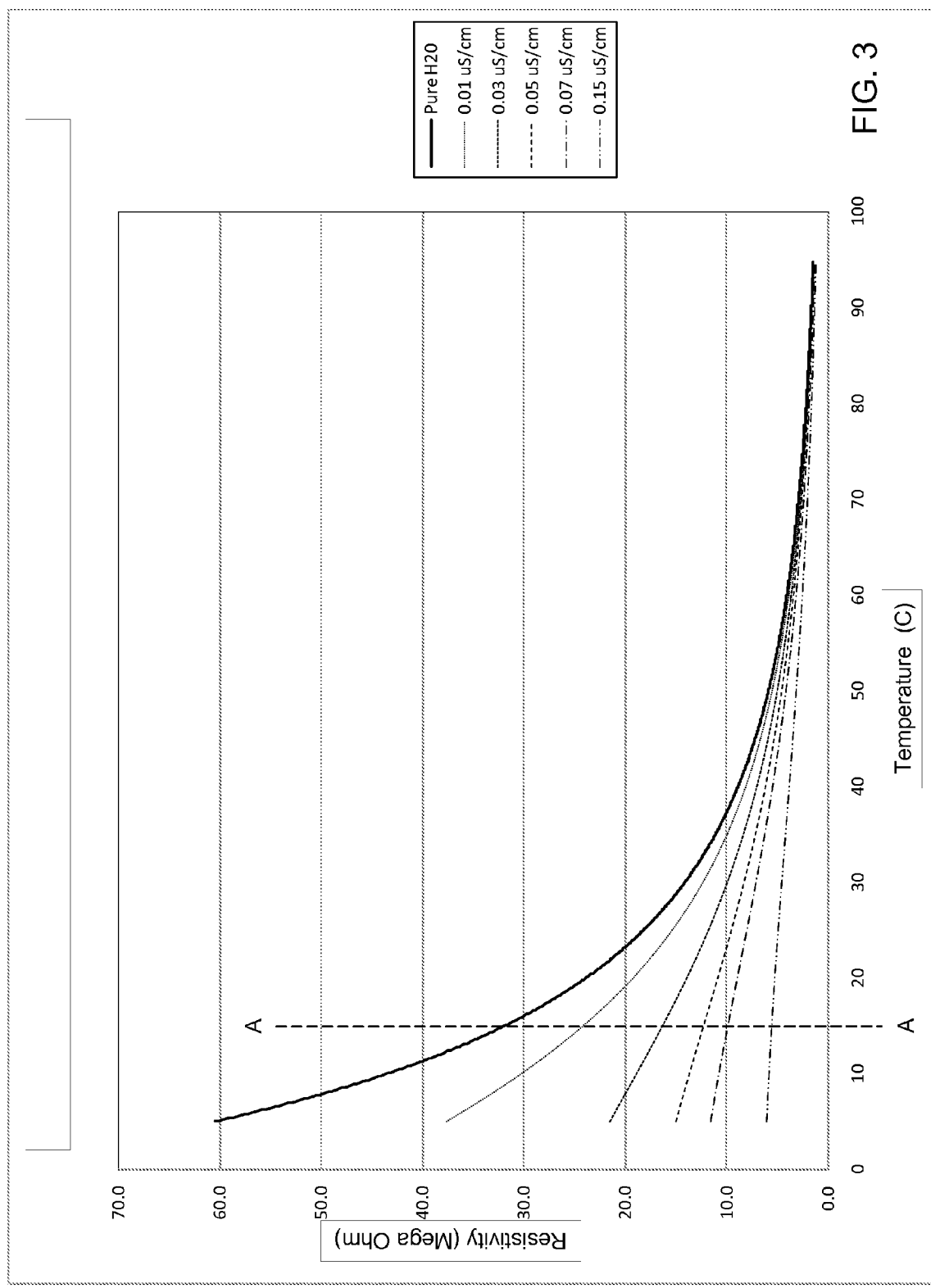
FIG. 3 is a simplified chart for use in the system of FIG. 1, depicting change in resistivity versus temperature for a theoretical water solution at various levels of contamination to include theoretically pure water.

FIG. 3 is exemplary chart depicting theoretical (or standardized) values for water solutions at various levels of contamination to include theoretically pure water. In FIG. 3, as indicated by the legend, each line corresponds to conductivity value ($C_{tca}$) (μLS/cm), which is intended to be indicative of the conductivity attributable only to the contaminants within the water solution. This conductivity value ($C_{tca}$) is intended to exclude conductivity attributable solely due to water molecules.

Using the chart (FIG. 3), the collected R/T slope can be compared to "theoretical" R/T slopes at the midpoint temperature ($T_{mid}$). The computing assembly 18 can use look-up tables towards that end. For example, based on the chart data of FIG. 3 along line A-A at 15 degrees Celsius, Table 1 depicts theoretical R/T slopes for water at various levels of contamination, in which contamination level is represented by a conductivity value (μS/cm) that accounts solely for the conductivity attributable to the contaminants, excluding any conductivity attributable to water molecules, as follows:

TABLE 1

Theoretically Determined Values for R/T Slope (dR/dT) and Conductivity ($C_{tca}$) (μS/cm) Attributable to Contamination, at 15° Celsius.
Temperature 15° C. (water)

| μS/cm | 0 | 0.001 | 0.002 | 0.003 | 0.004 | 0.005 | 0.006 | 0.007 | 0.008 | 0.009 |
|---|---|---|---|---|---|---|---|---|---|---|
| dR/dT | −1.91 | −1.80 | −1.69 | −1.51 | −1.42 | −1.35 | −1.28 | −1.21 | −1.15 | −1.10 |

At Step 20 (e), the system identifies the level of contamination, wherein the theoretical R/T slope matches the collected R/T slope at the midpoint temperature. Based on this comparing, an accurate value indicative of the contamination level of the water source 16 can be determined and provided (Step 20(e)). This contamination level can be expressed as a corresponding conductivity value (e.g., μLS/cm). For example, as shown in Table 1, if the collected R/T slope is −1.35 and the midpoint temperature is 15 degrees Celsius; then the corresponding conductivity ($C_{tca}$) (μS/cm) attributable to contamination is 0.005 μS/cm. Table 1 is provided as exemplary. The system 10 includes similar such data corresponding within a range of temperatures for the water source.

In this manner, a contamination level for the water source (16) can be expressed as a conductivity value.

Current industry standards often rely on resistivity values as indicative of contamination levels. Thus, for convenient reference, the system can provide, in addition or alternatively, at Step 20(e), a corresponding resistivity value (e.g., $R_{theory}$) indicative of the contamination level of the water source can be determined and provided. The system can use look-up tables towards that end as well. For example, Table 2 depicts conductivity values ($C_{tca}$) (μS/cm) and corresponding resistivity ($R_{theory}$) values (Mega Ω), at 15° Celsius:

TABLE 2

Theoretically Determined Values for Conductivity($C_{tca}$)(μS/cm) attributable to Contaminants and Corresponding Theoretical Resistivity Values ($R_{theory}$) (mega Ohm), for water at 15 degrees Celsius.
Temperature 15° C. (water)

| μS/cm | 0 | 0.001 | 0.002 | 0.003 | 0.004 | 0.005 | 0.006 | 0.007 | 0.008 | 0.009 |
|---|---|---|---|---|---|---|---|---|---|---|
| Mega Ω | 31.94 | 30.96 | 30.03 | 29.15 | 28.33 | 27.55 | 26.81 | 26.11 | 25.44 | 24.81 |

Table 2 is provided as exemplary. The system 10 includes similar such data corresponding within a range of temperatures for the water source. The resulting resistivity value ($R_{theory}$) is used to help determine the offset value, as discussed in more detail below.

In this example, theoretical values for water at various levels of contamination are provided via look-up charts or tables. However, such information can be captured in various other forms, formats, or manner, without departing from the invention. In addition or alternatively, the system can be configured to calculate such theoretical values.

In addition, or alternatively, at Step 20(e), the system assigns a new offset value ($OV_{new}$) for the resistivity sensor 14, based on the comparing of Step 20(d). Using Table 2, the system can arrive at a theoretical resistivity value based upon the midpoint temperature value and the corresponding conductivity value from Table 1, above. In the exemplary embodiment, the conductivity value determined from Table 1 is used to identify the corresponding theoretical, or standardized, resistivity value ($R_{theory}$), from Table 2. The resistivity offset value ($R_{offset}$) correlates to the difference between $R_{mid}$ and $R_{theory}$. Once the offset value is determined, it can be applied to the collected data set of Step (a) and/or to the filtered data set of Step (b), to provide highly accurate output measurement data.

In addition, or alternatively, the system can provide temperature corrected values for resistivity and/or conductivity. Current industry standards typically provide temperature corrected values at 25 degrees Celsius for water.

TABLE 3

Conductivity Value (μS/cm) attributable to Contaminants
and Resistivity Value (mega Ohm) at 25 degrees Celsius.
Temperature 25° C.

| μS/cm | 0 | 0.001 | 0.002 | 0.003 | 0.004 | 0.005 | 0.006 | 0.007 | 0.008 | 0.009 |
|---|---|---|---|---|---|---|---|---|---|---|
| Mega Ω | 18.18 | 17.86 | 17.54 | 17.24 | 16.95 | 16.67 | 16.39 | 16.13 | 15.87 | 15.63 |

At Step 20(f), the system resumes the process returning to Step 20(a) for a subsequent time interval. In the exemplary embodiment, the time intervals do not overlap. In addition, there is no break taken between time intervals. However, the time intervals can be spaced apart for prescribed durations without departing from the invention. Moreover, overlap between time intervals can be used.

With reference again to FIG. 1, the computing assembly 18 is configured to communicate and receive data from the temperature sensor 12 and the resistivity sensor 14. The connection among these components may be physical, fiber optic, wireless, or any other type of link, to include the Internet. Additionally, other types of communication means and protocols can be used, for example, a customer can transfer information by means of the memory card and memory card reader. It will be understood by those of ordinary skill in the art that other methods of communicating among the components can be used without departing from the invention.

The computing assembly 18 can be any number of combinations of one or microprocessors and digital memory devices configure to execute the method(s) embodied by the president invention, to include one or more personal computers, portable web-enabled devices, cloud-computing configurations, or other hardware and/or software combinations. For example, a personal computer operating a spreadsheet software program can be used. It will be understood by those of ordinary skill in the art that other methods of computing can be used without departing from the invention.

In the exemplary embodiments above, the systems and related methods in accordance with the invention are described in detail in which data and/or values, including "theoretical" values are accessed using lookup tables and/or graphs. However, it will be appreciated by those of ordinary skill in the art that various other means and methods of determining, accessing or calculating the relevant data and/or values can be used without departing from the invention, to include without limitation, e.g., histograms, bar graphs, algorithms, equations, or others, with no one being required to practice this invention, unless otherwise specified. In addition, slope values are discussed in relationship to change in resistivity versus change in temperature. In other embodiments, slope values (C/T slope) can be used, utilizing change in conductivity versus change in time, without departing from the invention.

In the exemplary embodiment, the system 10 is used in a process for producing high-purity water. The temperature sensor 12 and the conductivity/resistivity sensor 14 are positioned at prescribed locations along the process for purifying the water (or otherwise monitoring the purity of water). However, the system and method can be used in various other applications in which theoretical standard for resistivity versus temperature exists for a fluid and/or fluidic solution.

The system can be effectively used in wide variety applications for monitoring water purity. However, high purity water applications can have different temperature control strategies. Some applications tend to have more rapid and/or greater fluctuations in water temperature. The system can accommodate such variations, in a variety of manners, while achieving highly accurate measurements. For example, the time interval of data can be set such that some change in temperature of the water occurs over the prescribed time interval. For example, applications that do not change in temperature very rapidly can use relatively longer time intervals. Preferably, the time interval will capture a complete temperature cycle (high to low to high or vice versa. The system can further include in a heating mechanisms that cycles the water temperature at known intervals and ranges, to facilitate accuracy and predictability.

EXAMPLE

Figure 4:
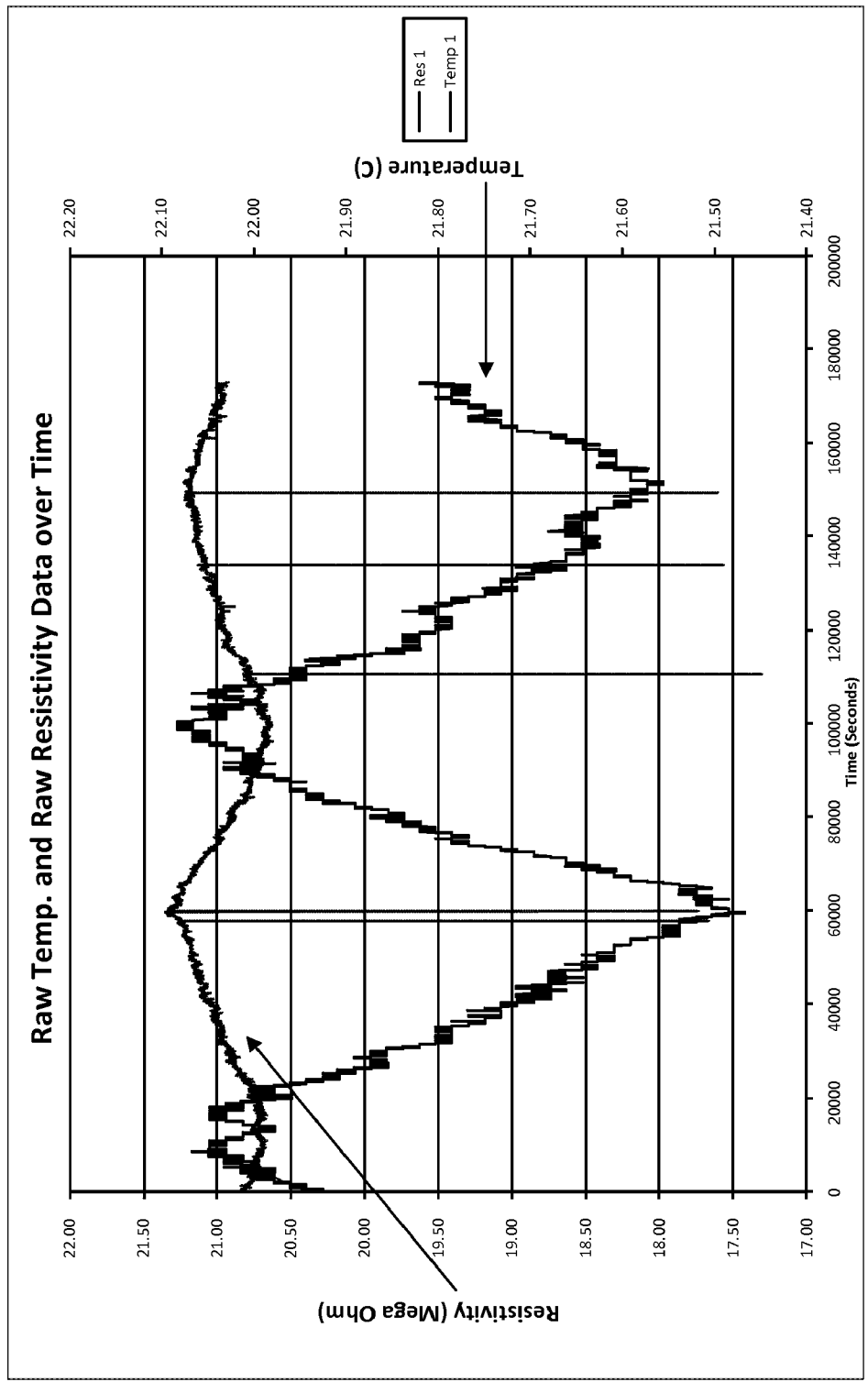
FIG. 4 is a simplified chart depicting an sample raw temperature data and resistivity data over time from an exemplary test conducted in accordance with the present invention

In an exemplary test, the system assembly includes a temperature sensor and a resistivity sensor exposed to a water flow in a water purification process, over time. A raw measurements for temperature and resistivity over a prescribed time interval as depicted in FIG. 4.

Figure 5:
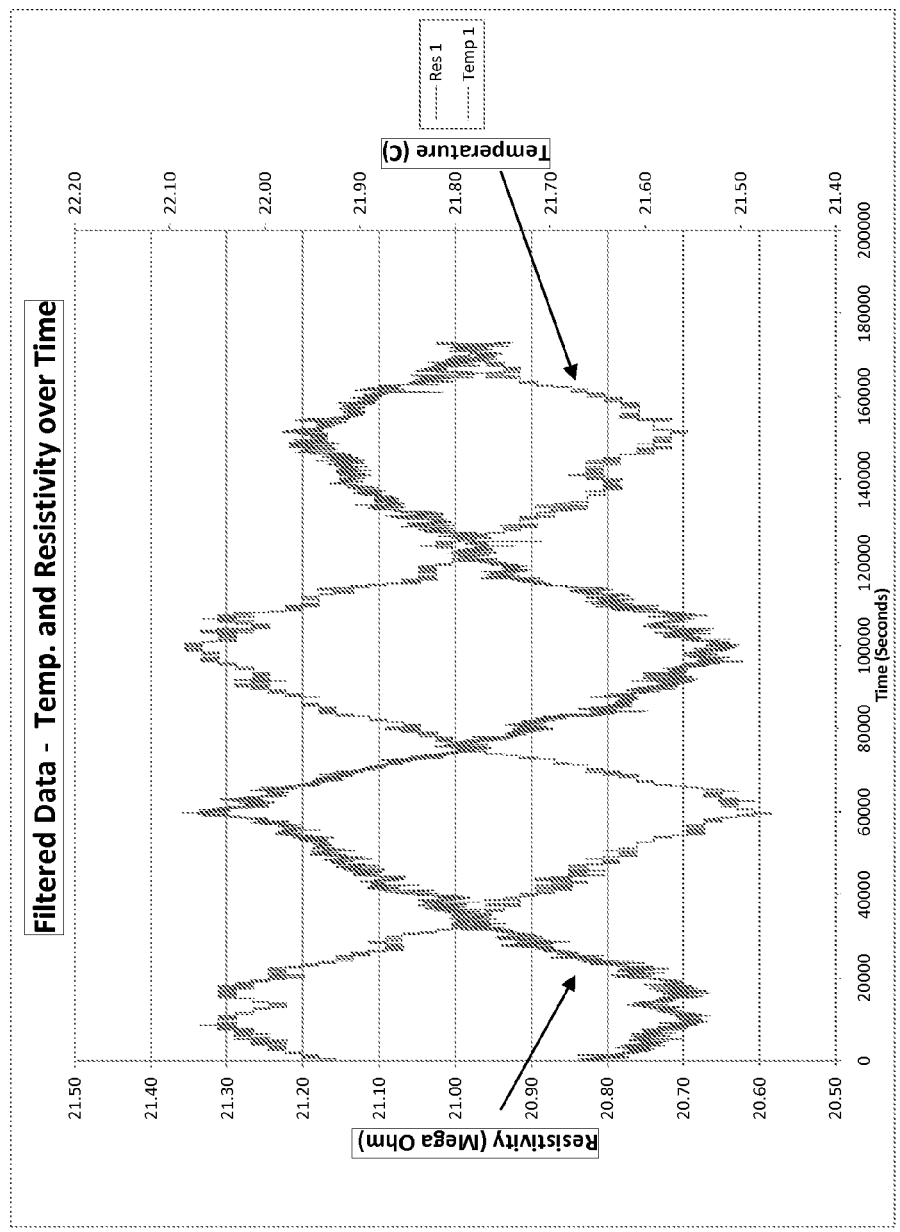
FIG. 5 is a simplified chart depicting a filtered data set from the raw data of the exemplary test of FIG. 4.

The data is filtered, by determining midpoint values for temperature and resistivity to exclude 'noise' measurements. In this example, median values are used. The midpoint resistivity ($R_{mid}$) is about 20.92 Mega Ω, and the midpoint temperature ($T_{mid}$) is about 21.73° C. The system filters out data that is outside of a prescribed range. The resulting filtered data set is shown in FIG. 5.

Figure 6:
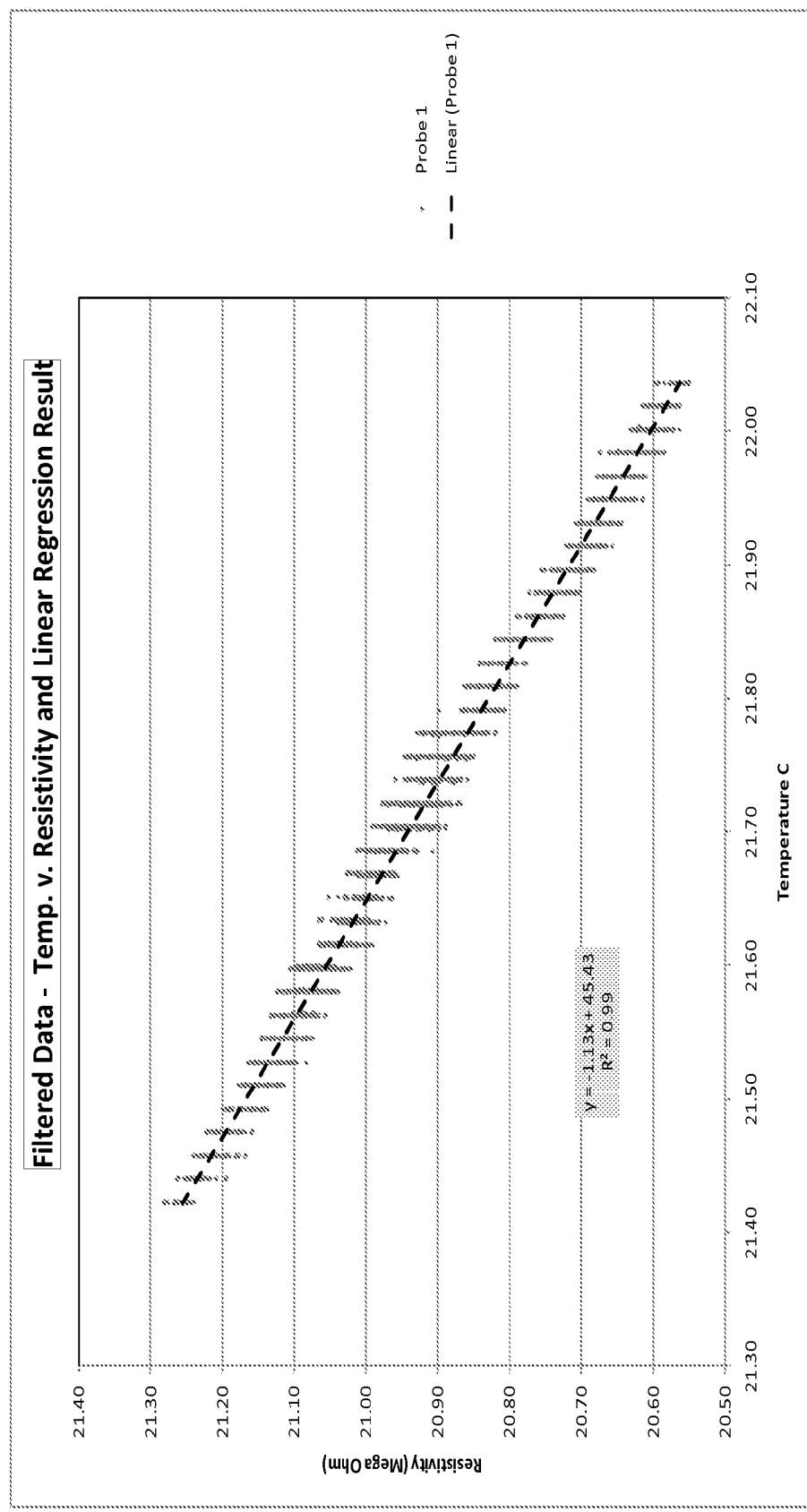
FIG. 6 is a simplified chart depicting a linear regression analysis applied to the filtered data set of FIG. 4, resulting in a collected R/T slope (dR/dT) value.
Figure 7:
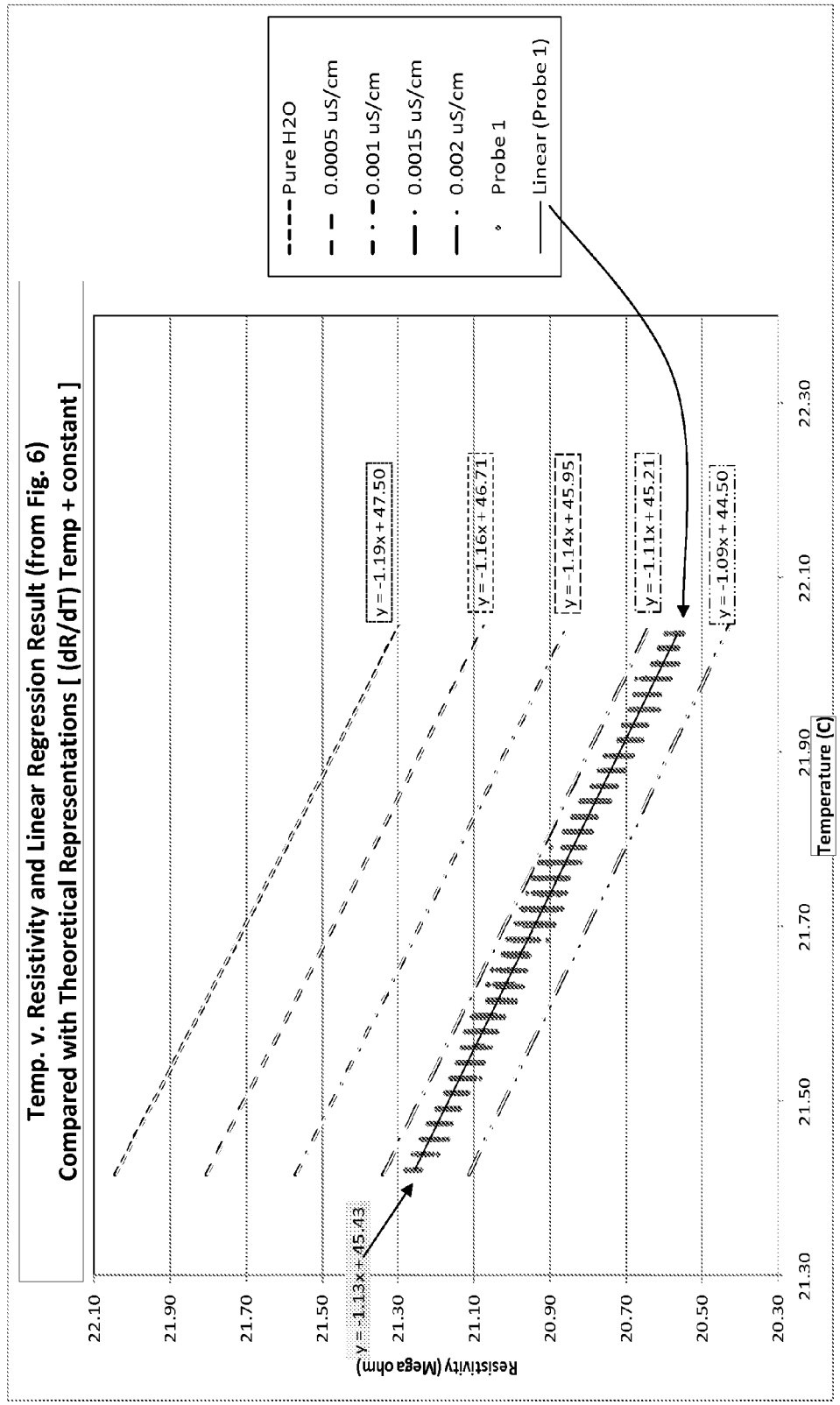
FIG. 7 is a simplified chart depicting the collected R/T slope of FIG. 6 compared to theoretical R/T slope values.
Figure 8:
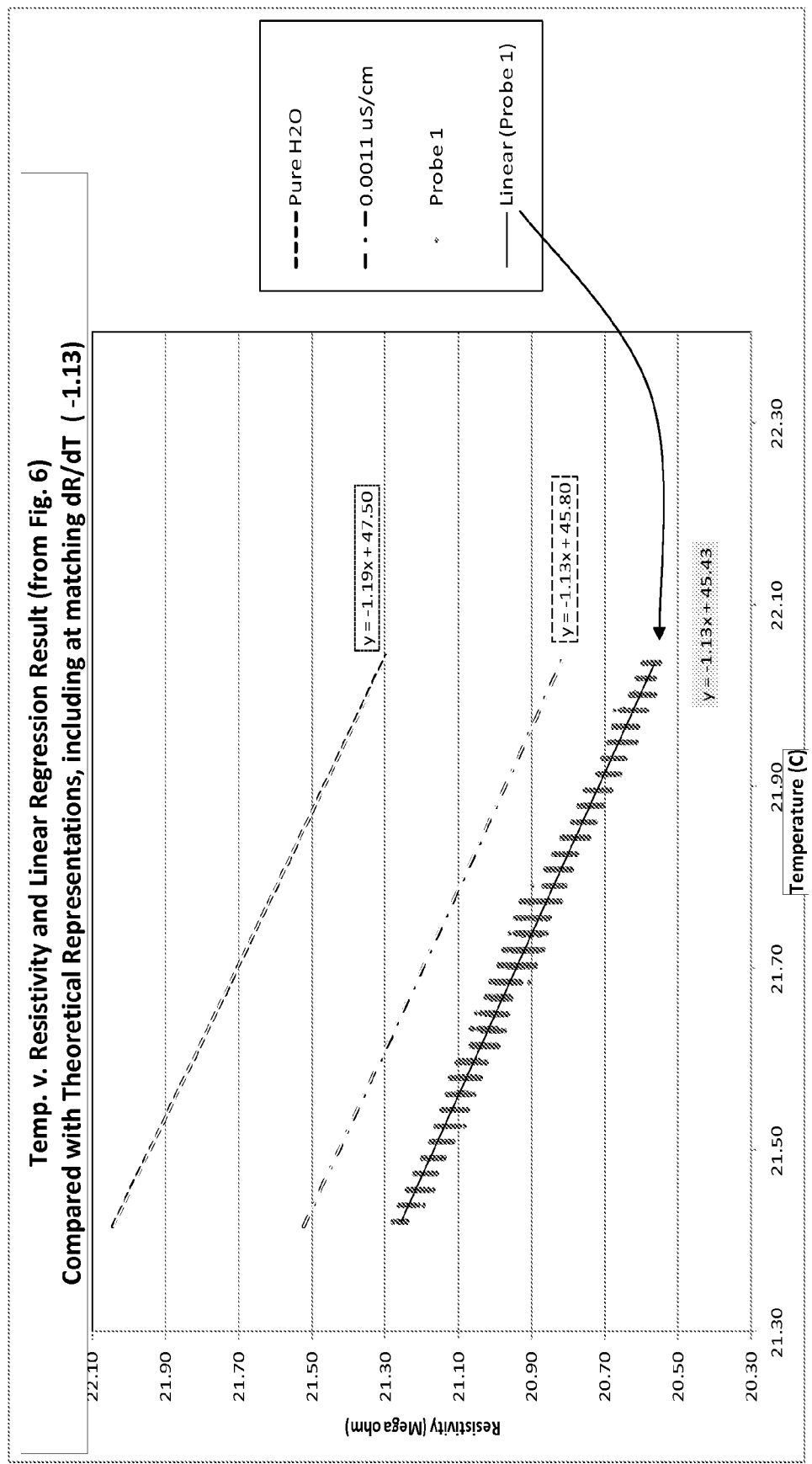
FIG. 8 is a simplified chart the collected R/T slope of FIG. 6 compared to theoretical R/T slope values, including a matching theoretical R/T slope.

As shown in FIG. 6, a least squares regression analysis is applied to the filtered data set, providing a collected R/T slope (dR/dT). The collected R/T slope is compared to theoretical R/T slope values, as shown in FIGS. 7 and 8, to find a matching theoretical R/T slope. As shown in FIG. 8, the collected R/T slope of −1.13 matches a theoretical R/T slope at conductivity value ($C_{tca}$) of 0.0011 μS/cm.

With reference now to FIG. 9, a table is shown, providing theoretical resistivity values in relation to temperature and to conductivity attributable to contamination. $R_{theory}$ can be determined by looking up the value at $T_{mid}$ (21.73° C.) and $C_{tca}$ (0.0011 μS/cm), providing an $R_{theory}$ value of 21.16 Mega Ω.

Figure 10:
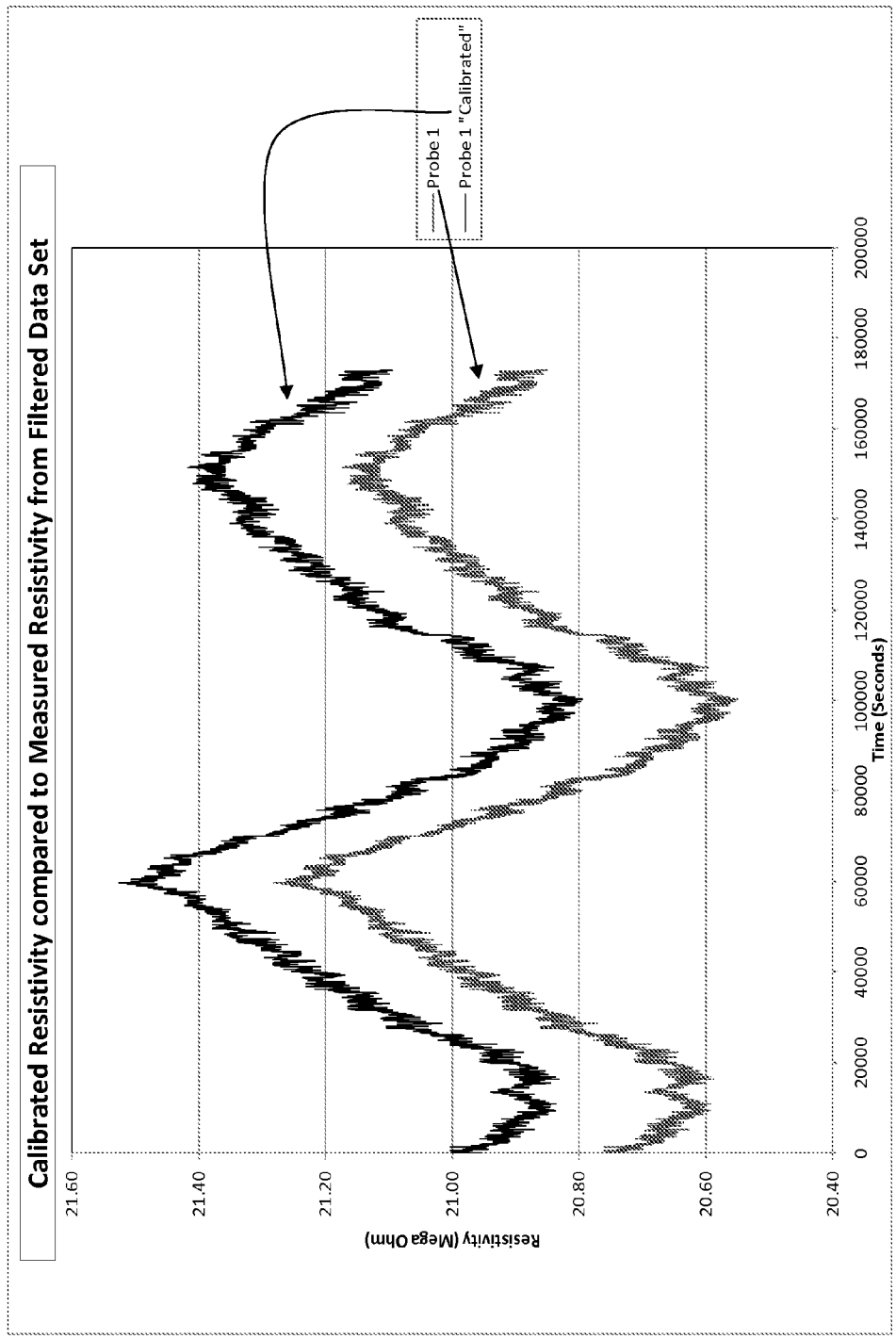
FIG. 10 is a simplified chart depicting calibrated resistivity values compared to measured resistivity from the filtered data from FIG. 4.

The resistivity offset value ($R_{offset}$) is determined as the difference between $R_{mid}$ and $R_{theory}$, which provides a resistivity offset value ($R_{offset}$) of −0.24 Mega Ω. The offset value can be applied to resistivity measurements from the filtered data set, to arrive at "calibrated" resistivity values, which are depicted in FIG. 10, for the present example. Accordingly, the system provides values calibrated continually during use, resulting in improved accuracy.

Although the invention has been disclosed in detail with reference only to the exemplary embodiments, those skilled in the art will appreciate that various other embodiments can be provided without departing from the scope of the invention. Accordingly, the invention is defined only by the claims set forth below.

What is claimed is:

1. A computerized method for measuring water having high purity, comprising:

collecting temperature measurements and resistivity measurements over a prescribed time interval from a temperature sensor and a resistivity sensor exposed to a water source;

determining, by a computing assembly, at least one of a midpoint for temperature ($T_{mid}$) and a midpoint for resistivity ($R_{mid}$), over the prescribed time interval;

determining, by the computing assembly, a collected R/T slope from the collected temperature measurements and the collected resistivity measurements, in which the collected R/T slope is indicative of the change in resistivity versus change in temperature as measured over the prescribed time interval;

comparing, by the computing assembly, the collected R/T slope to a standardized R/T slope at a temperature value corresponding to a midpoint temperature of the temperature measurements over the prescribed time interval; and providing, by the computing assembly, a compensated measurement for resistivity or conductivity of the water source based on the comparing.

2. A method as defined in claim 1, wherein the compensated measurement is a conductivity value that accounts solely for the conductivity attributable to contaminants within the water source.

3. A method as defined in claim 1, further comprising filtering out errant data from the collected temperature and collected resistivity measurements by discarding collected measurements in which the temperature measurement is outside of a prescribed range from the midpoint temperature, resulting in a filtered data set.

4. A method as defined in claim 3, wherein the collected R/T slope is determined from the filtered data set.

5. A method as defined in claim 4, wherein the collected R/T slope is determined using a linear regression on the filtered data set.

6. A method as defined in claim 1, further comprising, by the computing assembly, determining midpoint measurements for resistivity and temperature over the prescribed time interval.

7. A method as defined in claim 1, wherein the temperature sensor and the resistivity sensor are disposed in close proximity to one another.

8. A method as defined in claim 1, further comprising, by the computing assembly, determining a resistivity offset value based on the comparing.

9. A method as defined in claim 8, wherein the resistivity offset value is determined as the difference between the midpoint for resistivity ($R_{mid}$) and a theoretical value for resistivity ($R_{theory}$) determined based on the comparing.

10. A system for measuring water having high purity, comprising:

a temperature sensor exposed to a water source;

a resistivity sensor exposed to the water source proximate to the temperature sensor; and a computing assembly configured to receive measurement data from the temperature sensor and the resistivity sensor, the computing assembly configured for collecting temperature measurements and resistivity measurements over a prescribed time interval from a temperature sensor and a resistivity sensor exposed to a water source;

determining at least one of a midpoint for temperature ($T_{mid}$) and a midpoint for resistivity ($R_{mid}$), over the prescribed time interval;

determining a collected R/T slope from the collected temperature measurements and the collected resistivity measurements, in which the collected R/T slope is indicative of the change in resistivity versus change in temperature as measured over the prescribed time interval;

comparing the collected R/T slope to a standardized R/T slope at a temperature value corresponding to a midpoint temperature of the temperature measurements over the prescribed time interval; and providing a compensated measurement for resistivity or conductivity of the water source based on the comparing.

11. A system as defined in claim 10, wherein the computing assembly is further configured to filter out errant data from the collected temperature and collected resistivity measurements by discarding collected measurements in which the temperature measurement is outside of a prescribed range from the midpoint temperature, resulting in a filtered data set.

12. A system as defined in claim 10, wherein the computing assembly is further configured to determine and use a new resistivity offset value based on the comparing.

13. A system as defined in claim 12, wherein the resistivity offset value is determined as the difference between the midpoint for resistivity ($R_{mid}$) and a standardized value for resistivity ($R_{theory}$) determined based on the comparing.

14. A system as defined in claim 10, wherein the compensated measurement is a conductivity value that accounts solely for the conductivity attributable to contaminants within the water source.

15. A system as defined in claim 10, wherein the compensated measurement is a conductivity value that accounts solely for the conductivity attributable to contaminants within the water source.

16. A computerized method for measuring water having high purity, comprising:

collecting temperature measurements and resistivity measurements over a prescribed time interval from a temperature sensor and a resistivity sensor exposed to a water source, in which temperature measurements and resistivity measurements are associated together by time;

determining, by a computing assembly, midpoint measurements for resistivity ($R_{mid}$) and temperature ($T_{mid}$) over the prescribed time interval;

filtering out errant data from the collected temperature and resistivity measurements by discarding associated, collected measurements in which the collected temperature is outside of a prescribed temperature range, resulting in a filtered data set;

determining, by the computing assembly, a collected R/T slope from the filtered data set, in which the collected R/T slope is indicative of the change in resistivity versus change in temperature as measured over the prescribed time interval;

comparing, by the computing assembly, the collected R/T slope to a standardized R/T slope at a temperature value corresponding to a midpoint temperature of the temperature measurements over the prescribed time interval; and providing, by the computing assembly, compensated measurements for resistivity or conductivity of the water source based on the comparing.

17. A method as defined in claim 16, further comprising, by the computing assembly, determining midpoint measurements for resistivity and temperature over the prescribed time interval.

18. A method as defined in claim 16, further comprising, by the computing assembly, determining a resistivity offset value based on the comparing.

19. A method as defined in claim 16, wherein the compensated measurement is a conductivity value that accounts solely for the conductivity attributable to contaminants within the water source.

* * * * *